United States Patent [19]

Hall, II

[11] Patent Number: 4,583,859

[45] Date of Patent: Apr. 22, 1986

[54] FILTER CLEANING SYSTEM FOR OPACITY MONITOR

[75] Inventor: George R. Hall, II, Wickliffe, Ohio

[73] Assignee: The Babcock & Wilcox Company, New Orleans, La.

[21] Appl. No.: 595,205

[22] Filed: Mar. 30, 1984

[51] Int. Cl.$^4$ ............................................. G01N 21/15
[52] U.S. Cl. ..................................... 356/438; 55/287; 250/236; 250/573
[58] Field of Search ............... 356/437, 438, 439, 440; 350/584; 250/236, 573, 575; 55/287, 286, 285, 288

[56] References Cited

U.S. PATENT DOCUMENTS

| | | | |
|---|---|---|---|
| 1,784,339 | 12/1930 | Clasen et al. | 55/287 X |
| 1,969,626 | 8/1934 | Simon et al. | 356/438 |
| 2,796,950 | 6/1957 | Hersey | 55/287 |
| 3,777,458 | 12/1973 | Dence | 55/287 |
| 3,803,814 | 4/1974 | Parsons | 55/287 |
| 3,826,577 | 7/1974 | Irwin | 356/438 |
| 3,932,040 | 1/1976 | Warncke | 250/573 X |
| 3,973,852 | 8/1976 | Moore et al. | 356/438 |
| 3,994,601 | 11/1976 | Brugger | 356/438 |
| 4,247,205 | 1/1981 | Typpo | 356/438 |
| 4,381,153 | 4/1983 | Bohl et al. | 250/236 X |

Primary Examiner—Vincent P. McGraw
Assistant Examiner—Robert D. V. Thompson, III
Attorney, Agent, or Firm—Vytas R. Matas; Robert J. Edwards

[57] ABSTRACT

A filter cleaning system for an opacity monitor which has a light source and a light sensor on opposite sides of a first optical path through a gas whose opacity is to be measured, comprises a mechanism for calibrating the opacity monitor during a calibration period and a purging air arrangement for supplying purging air to pipes in the first optical path to keep the interior of the pipes clean. A primary filter is connected to the blower for filtering the purging air. Three-way valves are connected to the input and the output of the blower so that a secondary filter can be utilized to supply clean air in a reverse flow through the primary filter to clean the primary filter. The primary filter is cleaned during this blow-down period at the same time that calibration is taking place for the opacity monitor. In this way, no measuring time is wasted and still the life of the primary filter is extended.

5 Claims, 3 Drawing Figures

TIMING SEQUENCE

FILTER CLEANING SYSTEM FOR OPACITY MONITOR

FIELD AND BACKGROUND OF THE INVENTION

The present invention relates, in general, to opacity monitors for monitoring the amount of light passing through a gas, in particular for determining how much smoke is being emitted from a stack, and in particular to a new and useful filter cleaning system for such opacity monitors Monitors are known for measuring how much light is blocked by gases passing through a conduit or stack. A light source and a light sensor lie on opposite sides of an optical path through the conduit or stack. This measurement of opacity for the gases is a measurement of the amount of particles or smoke in the gas.

Part of the optical path between the light source and light sensor is shielded by a pipe to avoid contamination of optic windows separating the light source and sensor from the contaminating environment of the conduit or stack. It is known to supply purging air to the pipes for keeping the optical windows clean and free of soiling or abrasion by particles in the conduit or stack being monitored. Such damage or contamination to the optical windows would produce false opacity readings.

It is known to first filter the purging air through two- and three- stage filters. These filters must frequently be cleaned and changed manually.

SUMMARY OF THE INVENTION

The present invention comprises a filter cleaning system for an opacity monitor which has microprocessor electronics that automatically calibrate the optics periodically, and at the same time, cause a cleaning cycle for the filters. This greatly extends filter life and utilizes calibrating time during which purging air is not needed.

Accordingly, an object of the present invention is to provide a filter cleaning system for an opacity monitor having a light source and a light sensor on opposite sides of a first optical path for measuring the opacity of gas in the first optical path, comprising, calibration means operatively connected to the light source and sensor for calibrating the opacity monitor during a calibration period, a pair of protective pipes having facing open ends and lying on the first optical path between the light source and sensor with gas whose opacity is to be measured, adapted to pass between the open ends, a blower having an input for receiving air and an output for supplying air, a primary filter for filtering air to be supplied to the blower, valve means connected to the blower, to the primary filter and to the pair of protective pipes, having a first position for supplying purging air from the filter to the blower and from the blower to the protective pipes for purging the protective pipes, and a second position for supplying blow-down air through the blower to the primary filter for cleaning the primary filter and control means connected to the calibration means and to the valve means for moving the valve means into its second position when the calibration means is activated to calibrate the opacity monitor during the calibration period.

A further object of the invention is to provide the calibration means with a second optical pathway containing air or a gas with substantially zero opacity, and transfer means for transferring the light source and sensor from the first optical pathway to the second optical pathway.

A still further object of the invention is to provide such a filter cleaning system wherein simple function blocks are combined to achieve the functions of initiating a calibration period and a blow-down period as well as calibrating the opacity monitor. A still further object of the invention is to provide a filter cleaning system which is simple in design, rugged in construction and economical to manufacture.

For an understanding of the principles of the invention, reference is made to the following description of a typical embodiment thereof as illustrated in the accompanying drawings.

DESCRIPTION OF THE PREFERRED EMBODIMENT

Figure 1:
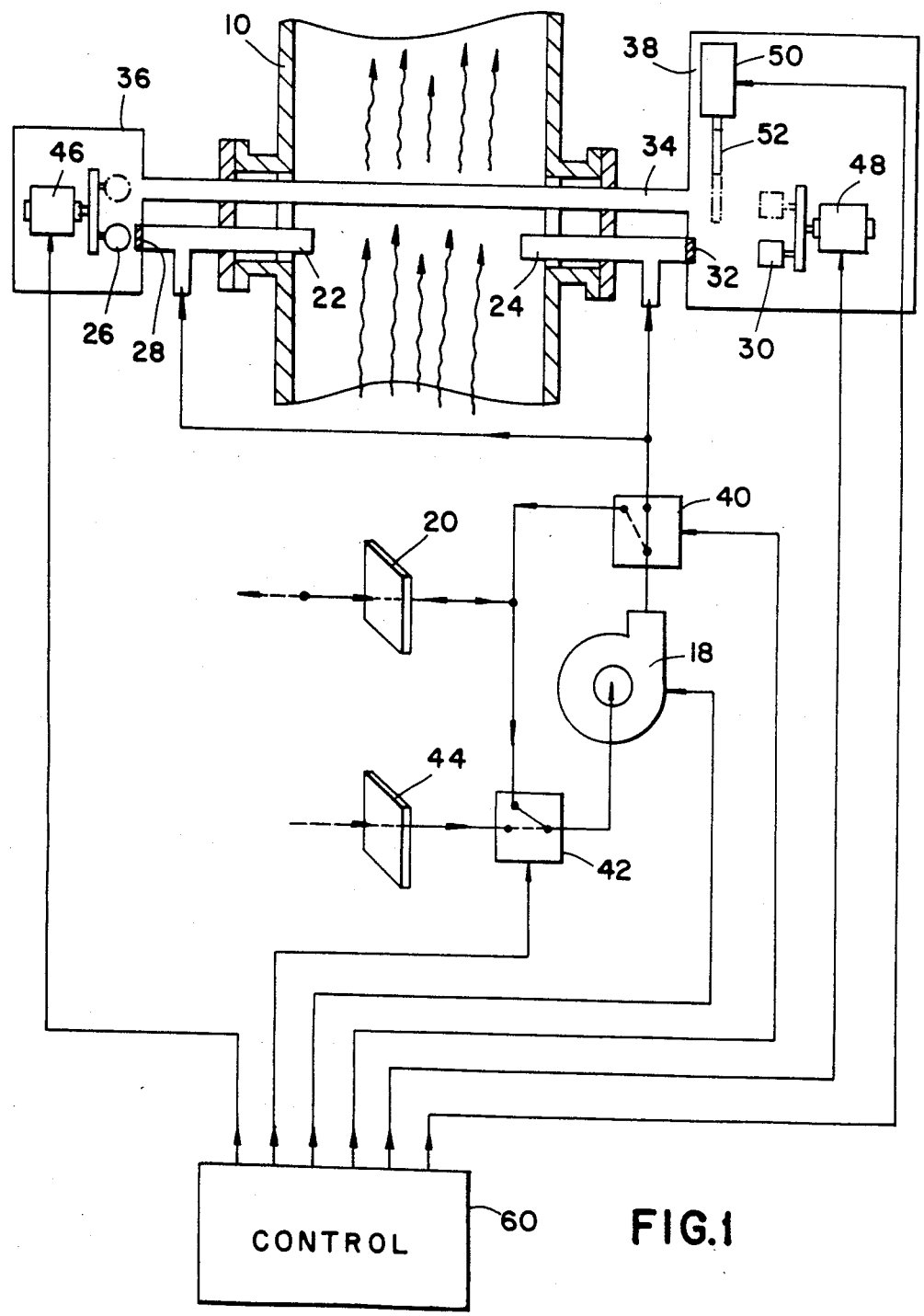
FIG. 1 is a schematic representation of an optical monitor incorporating the filter cleaning system of the invention.

Referring to the drawings, in particular, the invention embodied in FIG. 1 comprises a filter cleaning system for an opacity monitor which effects an automatic and periodic cleaning of a primary intake filter 20 during a calibration period for the opacity monitor. While shown as a single filter, primary intake filter 20 can incorporate several filter stages.

The opacity monitor is used in conjunction with a conduit or stack 10 for determining the opacity of gases or smoke flowing through the stack, and in the upward direction in FIG. 1. A first optical pathway is defined through the stack 10 by spaced-apart and axially aligned pipes 22 and 24 which have open facing ends. Light is supplied by a light source 26 through an optical window 28, and through the stack 10, to a light sensor 30. Light sensor 30 is also isolated from the gases in stack 10 by a second optical window 32. For purposes of calibration, a "0" pipe 34 extends through the stack and defines a second optical pathway. The air within pipe 34 as well as in housing 36 for the light source and housing 38 for the light sensor are maintained under clean conditions so that the opacity of the air in the second pathway is assumed to be zero. That is, the air is assumed to be substantially transparent.

As is known, clean purging air is supplied to the interior of pipes 22 and 24 near the side of the optical windows 28, 32 which are exposed to the contaminating gases in stack 10. This air is drawn through primary filter 20 by a blower 18.

In accordance with the invention, two three-way valves 40 and 42 separate the output and input of blower 18 from the pipes 22, 24 and the filter 20 respectively. During a "blow-down" period, filter 20 is backwashed with air which is also supplied by blower 18 over the dotted line pathway in three-way valves 40, 42. Clean air for the blow-down or filter cleaning period is provided through a secondary filter 44 which is, during this period, connected to the input of blower 18, the output of blower 18 being connected to filter 20.

The blow-down period is chosen to correspond to a calibration period during which the opacity monitor is calibrated.

Calibration of the opacity monitor is achieved by utilizing motors 46 and 48 which are respectively connected to the light source 26 and the sensor 30. Motors 46, 48 are activatable to rotate their shafts by 180° to move both the light source and the light sensor from the first optical path to the second optical path, that is, into alignment with the zero pipe 34. This is shown in a phantom line position in FIG. 1. In this way, a zero opacity signal $O_O$ can be produced in sensor 30 which corresponds to the measurement of zero opacity for the air in zero tube 34.

Calibration filter means 50 is also provided for moving a calibrated neutral density range filter 52 into the second optical pathway between the light source and sensor. The calibration filter has a known optical value $O_D$ and produces an opacity signal $O_C$. In this way, a calibration factor $O_F$ can be calculated utilizing measurements with the filter in and out of the second optical path. The relationship is:

$$O_F = \frac{O_c - O_o}{O_D} \tag{1}$$

$$O_P = \frac{O_M - O_o}{O_F} \tag{2}$$

$$O_s = 1 - (1 - O_p)^F \tag{3}$$

After the calibration period, motors 46, 48 are activated to return the light source and sensor to the first optical pathway defined between pipes 22, 24. In this position, sensor 30 generates a measured opacity value $O_M$ which corresponds to the measured opacity of the smoke or gas passing through conduit or stack 10.

As will be explained later, the true opacity $O_P$ can be calculated according to the relationship:

$$O_p = \frac{O_M - O_o}{O_F}. \tag{2}$$

From this true opacity value at the measured light path, a true opacity at the stack outlet $O_S$ can be determined according to the relationship:

$$O_S = 1 - (1 - O_P)^F \tag{3}$$

Where F is the stack factor and equals the mean diameter of the stack outlet, that is the diameter of the outlet of conduit 10, divided by the length of the measurement path, that is the distance between the ends of pipes 22 and 24.

Three-way valves 40 and 42 are moved from their solid line position to their dotted line position during the blow-black or filter cleaning phase. This is done in appropriate timing with activation of motors 46 and 48 as well as activation of the filter means 50. These controllable elements as well the light source 26 and the sensor 30 are connected to a control 60.

The controlling functions of control 60 will now be explained in conjunction with FIGS. 2 and and 3.

Figure 2:
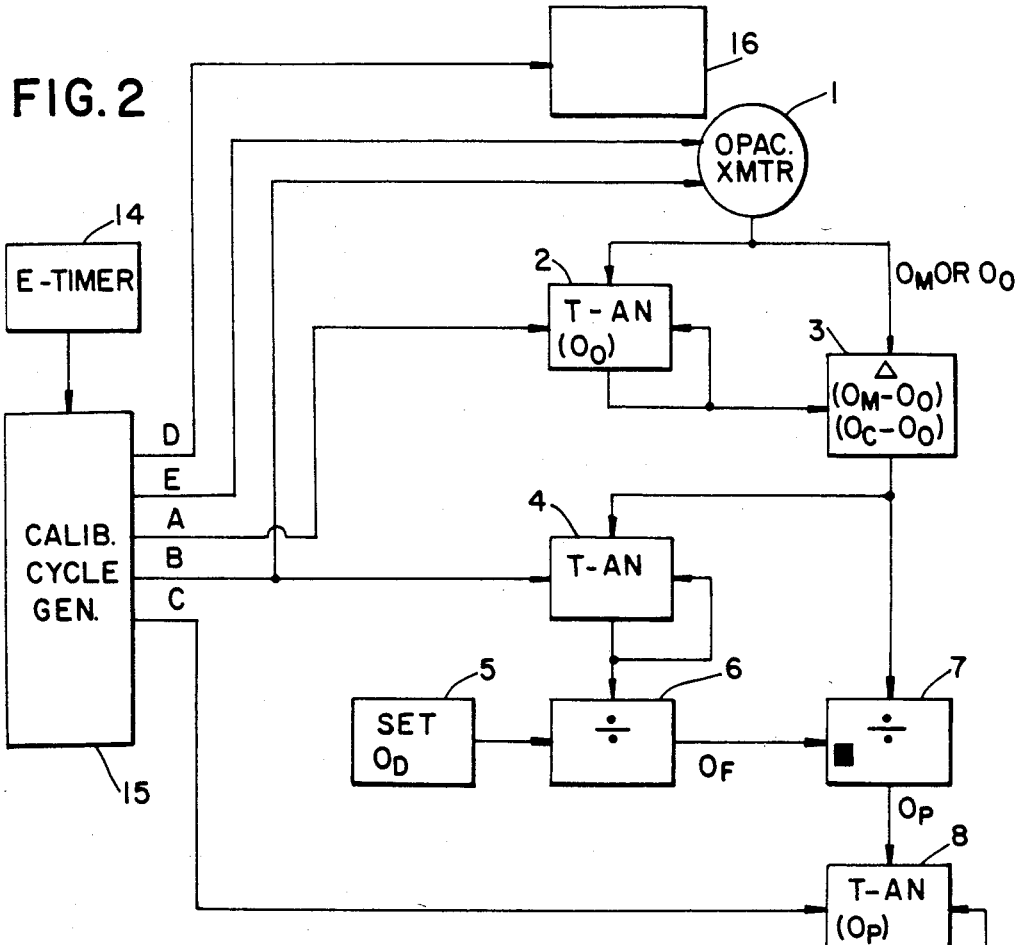
FIG. 2 is a block diagram showing part of the control arrangement for the filter cleaning system of the invention.

In FIG. 2, a timer 14 for generating signals when a calibration and filter cleaning operation should be instituted, is connected to a calibration cycle generator 15.

Calibration cycle generator 15 executes a sequence of operations to effect calibration and filter-cleaning.

Figure 3:
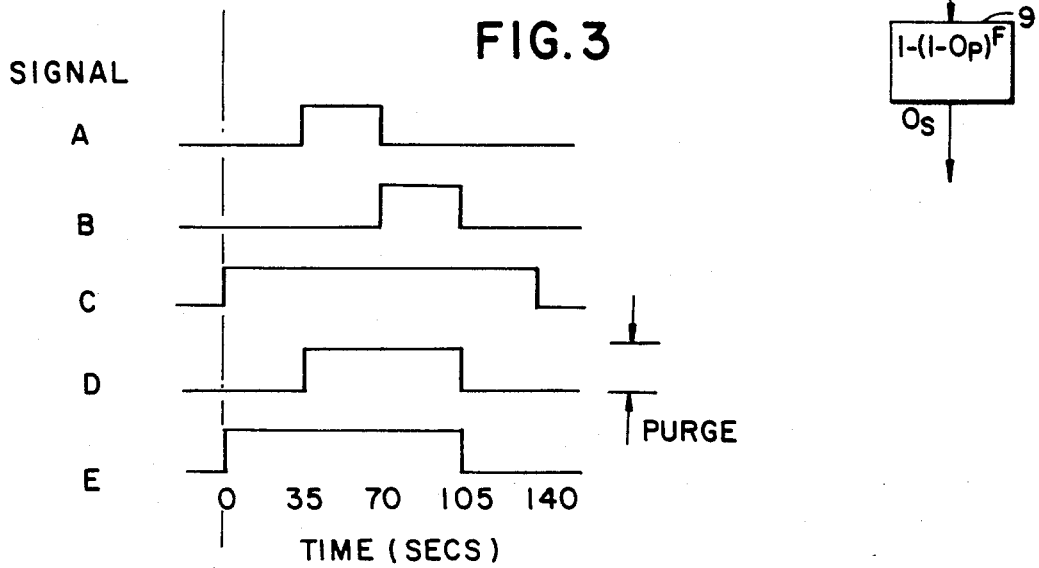
FIG. 3 is a timing diagram showing when various operations in the invention begin and stop.

At zero time as illustrated in FIG. 3, outputs C and E change from logical zero to logical one. Output C is connected to a transfer function block 8 which holds the system output value, that is the true opacity measurement $O_P$ as its last value during the calibration cycle. Output E is connected to opacity transmitter 1 which, in turn, is connected to the light sensor 30 as well as to the motors 46 and 48 to move the light source and sensor head from the first light pathway to the second light pathway, that is the phantom line representations in FIG. 1 which are in alignment with the zero pipe 34.

The transfer is completed within 35 seconds after which the next step can be taken.

At 35 seconds outputs A and D change from logical zero to logical one. Output A is connected to transfer function block 2 which takes the zero opacity signal reading $O_O$ which is now being generated by sensor 30 and supplied by opacity transmitter 1 to the function block 2.

Output D initiates the purge system filter blowdown cycle as it is connected to purge means 60 which is connected and controls the three-way valves 40 and 42 to start the flow of fresh purging air from filter 44 to filter 20.

The zero opacity signal stabilizes within 35 seconds and blow-down continues during this interval.

At 70 seconds, output A changes from logical one to logical zero. This causes function block 2 to hold its last zero opacity signal $O_O$. At this point, output B changes from logical zero to logical 1. Output B is connected both to the opacity transmitter 1 as well as to a transfer function block 4. Opacity transmitter 1 is also connected to the calibration means 50 and signal B activates movement of calibration neutral density range filter 52 into the second optical pathway and thus in front of zero pipe 34. It is noted that filter means 50 with filter 52 might be positioned elsewhere on the second optical pathway, that is closer to light source 26.

Output B also activates transfer function block 4 to read the output of a function block 3 which takes the difference between the unscaled calibrated signal $O_C$ and the zero value signal $O_O$. The unscaled signal is provided by sensor 30 over transmitter 1 and the zero value is provided from the function block 2. The output of function block 4 represents the range value of the opacity signal corrected for true zero. This signal stabilizes within the interval from 70 to 105 seconds as shown in FIG. 3. At 105 seconds, signals B, D and E change from logical one to logical zero. Signal D transfers the purge system 16 from its "blow-down" stage to its "purge" stage. This is done by switching three-way valves 40 and 42 back to their solid line position which allows blower 18 to supply filtered air from filter 20 to the pipes 22 and 24.

Simultaneously with this output B, signals the transfer function block 4 to hold its last value and causes transmitter 1 to activate filter means 50 to remove filter 52 from the second optical pathway.

The transfer occurs and the opacity measurement stabilizes within the interval from 105 to 140 seconds.

At 140 seconds, output C changes from logical one to logical zero. This signals transfer function block 8 to read the opacity signal from function block 7. Function blocks 7 and 6 are dividing units. Function block 6 is connected to a set point block 5 which contains the known opacity value $O_D$ for the neutral density filter. This is divided by the output from function block 4. The output of function block 6 is thus equal to the calibration factor $O_F$ in accordance with equation (1) above. Function block 7 operates to calculate true opacity $O_P$ in accordance with equation (2). This is because transfer out of the calibration phase causes transmitter 1 to supply the measured opacity $O_M$ which is generated in sensor 30.

A "power" function block 9 is connected to the output of function block 8 to generate the true opacity $O_S$ in accordance with equation (3). Note that the stack factor F is a known and constant value which is incorporated into block 9. The output of block 9 could be used in any known fashion and as part of the usual stack electronics.

While a specific embodiment of the invention has been shown and described in detail to illustrate the application of the principles of the invention, it will be understood that the invention may be embodied otherwise without departing from such principles.

What is claimed is:

1. A control system for coordinating the calibration and filter cleaning functions in an opacity monitor having a light source and a light sensor on opposite sides of a first optical path for measuring the opacity of a gas in the first optical path, comprising:
   calibration means operatively connected to the light source and sensor for calibrating the opacity monitor during a calibration period;
   a pair of protective pipes having facing open first ends and lying on the first optical path between the light source and sensor with the gas whose opacity is to be measured adapted to pass between said open first ends;
   a blower having an input for receiving air and an output for supplying air;
   a primary filter for supplying filtered air for purging said protective pipes;
   a secondary filter for supplying filtered blowdown air for blowdown cleaning of said primary filter;
   valve means connected to said blower input and output, to said primary filter and to said pair of protective pipes, having a first position for supplying purging air from said primary filter to said blower input and from said blower output to said protective pipes for purging said protective pipes, and a second position for supplying blowdown air from said secondary filter to said blower input and from said blower output to said primary filter for cleaning said primary filter; and
   control means connected to said calibration means and to said valve means for moving said valve means into said second position thereof when said calibration means is activated to calibrate the opacity monitor during said calbration period.

2. A control system according to claim 1, wherein said calibration means includes a second optical pathway, a zero pipe extending along said second optical pathway for maintaining substantially zero opacity along said second optical pathway, transfer means connected to said light source and light sensor for transferring said light source and light sensor between said first and second optical pathways, calibration filter means including a calibration filter with known opacity, for moving said calibration filter into said second optical pathway, said control means connected to said transfer means and to said calibration filter means for transferring said light source and sensor from said first optical pathway to said second optical pathway during the beginning of said calibration period and, during some point of said calibration period, moving said calibration filter into said second optical pathway.

3. A control system according to claim 2, wherein said control means includes a calibration cycle generator, an opacity transmitter connected to said light sensor, to said transfer means and to said calibration filter means for receiving a signal form said light sensor and for activating said transfer means and said calibration filter means, a first transfer function block connected to said opacity transmitter for receiving a signal from said light sensor, a difference block connected to said opacity transmitter and to said first function block for taking a difference between a signal from said first function block and a signal from said light sensor, a second transfer function block connected to an output of said difference block, and calculation means connected to an output of said second function block and the output of said difference block for calculating a true opacity of the gas adapted to move through said first optical path as a function of a zero opacity reading taken on said second optical path, as known opacity reading taken through said calibration filter and a dimensional factor which is a function of the distance between said open first ends of said protective pipes, said calibration cycle generator including timing means and having a first output connected to said first function block for taking the zero opacity reading, a second output connected to said opacity transmitter and to said second function block for activating said calibration filter means and taking said known opacity reading, a third output connected to said calculation means for initiating said true opacity calculation, a fourth output connected to said valve means for initiating cleaning of said primary filter and a fifth output connected to said opacity transmitter for activating said transfer means for initiating said calibration period.

4. A control system according to claim 3, wherein said calculation means comprises a first division unit having a first input connected to said second transfer function block and a second input connected to setting means containing a value corresponding to the known opacity of said calibration filter, a second divison unit connected to an output of said first division unit and an output of said difference block for measuring a difference between the zero opacity reading and the known opacity reading, and for measuring the difference between a measured opacity reading through said first optical path and said zero opacity reading, and a third transfer function block connected to an output of said second division unit and said third output of said calibration cycle generator for measuring a true opacity measurement as a function of said measured opacity reading, said zero opacity reading and the known opacity of said calibration filter.

5. A control system according to claim 4, wherein said valve means comprises:
   a first three-way valve having an input connected to said blower output, a first output connected to said protective pipes and a second output connected to said primary filter;
   a second three-way valve having an output connected to said blower input, a first input connected to said primary filter and a second input for receiving air from said secondary filter;

said first and secnd three-way valves being connected to said fourth output of said calibration cycle generator, said first three-way valve having its input connected to its first output and said second three-way valve having its output connected to its first input with said valve means being in said first position thereof, and said first three-way valve having its input connected to its second output and said second three-way valve having its output connected to its second input with said valve means in the second position thereof.

* * * * *